United States Patent
Miller et al.

(10) Patent No.: US 6,911,180 B2
(45) Date of Patent: *Jun. 28, 2005

(54) CATALYTIC SENSOR

(75) Inventors: James B. Miller, Pittsburgh, PA (US); Celeste Hort, Cranberry Township, PA (US); Towner B. Scheffler, Butler, PA (US)

(73) Assignee: Mine Safety Appliances Company, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/691,003

(22) Filed: Oct. 22, 2003

(65) Prior Publication Data

US 2004/0241870 A1 Dec. 2, 2004

Related U.S. Application Data

(63) Continuation of application No. 09/698,740, filed on Oct. 27, 2000, now Pat. No. 6,663,834.

(51) Int. Cl.[7] .................. G01N 31/12; G01N 27/00; G01N 27/16; G01N 9/00; G01N 19/10
(52) U.S. Cl. .................. 422/94; 422/83; 422/88; 422/95; 422/96; 422/97; 422/98; 73/1.01; 73/1.02; 73/23.2; 436/149; 436/156; 436/155; 436/159
(58) Field of Search .................. 422/83, 88, 94, 422/95, 96, 97, 98; 73/1.01, 1.02, 23.2; 436/149, 156, 155, 159

(56) References Cited

U.S. PATENT DOCUMENTS 5,804,703 A * 9/1998 Wind et al. ............... 73/25.01
5,922,287 A * 7/1999 Kato et al. ................... 422/95

* cited by examiner

Primary Examiner—Jill Warden
Assistant Examiner—Brian Sines
(74) Attorney, Agent, or Firm—James G. Uber; Henry E. Bartony, Jr.

(57) ABSTRACT

A combustible gas sensor includes an active element in electrical connection with a measurement circuit. The measurement circuit includes a thermistor network to compensate for the effect of changes in ambient temperature to the resistance of the active element. Another combustible gas sensor includes an active element having a geometric surface area no greater than approximately 0.5 mm$^2$ in electrical connection with a measurement circuit. The measurement circuit includes a compensator that compensates for the effect of changes in ambient temperature to the resistance of the active element without compensating for heat lost by thermal conduction from the active element. A method of sensing gas including the steps of: (i) providing a catalytic active element having a geometric surface area sufficiently small such that the effect upon the output of the active element of heat lost from the active element by thermal conduction is relatively small, and (ii) compensating for only the effect of changes in ambient temperature upon the output of the active element.

20 Claims, 6 Drawing Sheets

CATALYTIC SENSOR

This is a continuation of application Ser. No. 09/698,740, filed Oct. 27, 2000, now U.S. Pat. No. 6,663,834.

FIELD OF THE INVENTION

The present invention relates to catalytic sensors, and, particularly, to catalytic sensors in which a conventional compensating element is eliminated.

BACKGROUND OF THE INVENTION

Catalytic or combustible (flammable) gas sensors have been in use for many years to, for example, prevent accidents caused by the explosion of combustible or flammable gases. In general, combustible gas sensors operate by catalytic oxidation of combustible gases. As illustrated in FIG. 1A, a conventional combustible gas sensor 10 typically includes a platinum element or coil 20 encased in a refractory (for example, alumina) bead 30, which is impregnated with a catalyst (for example, palladium or platinum) to form an active pelement 40 or pellistor. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensor are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

In general, pelement 40 operates as a small calorimeter which measures the energy liberated upon oxidation of a combustible gas. A portion of the energy released during the oxidation reaction is absorbed by bead 30, causing the temperature of bead 30 to rise. In response to the temperature increase, the electrical resistance of platinum element 20 also increases. At constant applied current, the resistance increase is measured as an increase in voltage drop across element 20. Platinum element 20 serves two purposes within pelement 40: (1) heating bead 30 electrically to its operating temperature (typically approximately 500° C.) and (2) detecting the rate of oxidation of the combustible gas.

Bead 30 will react to phenomena other than catalytic oxidation that can change its temperature (i.e., anything that changes the energy balance on the bead) and thereby create errors in measurement of combustible gas concentration. Among these phenomena, most important in terms of the magnitude of their effect are changes in ambient temperature and thermal diffusion or conduction from bead 30 through the analyte gas. Other factors typically have less of an impact.

To minimize the impact of secondary, thermal effects on sensor output, the rate of oxidation of the combustible gas may be measured in terms of the variation in resistance of the platinum element 20 relative to a reference resistance embodied in an inactive, compensating pelement 50. The two resistances are generally part of a measurement circuit such as a Wheatstone bridge circuit as illustrated in FIG. 1B. The output or the voltage developed across the bridge circuit when a combustible gas is present provides a measure of the concentration of the combustible gas. The characteristics of compensating pelement 50 are typically matched as closely as possible with active pelement 40. Compensating pelement 50, however, typically either carries no catalyst or carries inactivated catalyst.

Typically, active pelement 40 and the compensating pelement 50 are deployed within wells 60A and 60B of an explosion-proof housing 70 and are separated from the surrounding environment by a flashback arrestor, for example, a porous metal frit 80. Porous metal frit 80 allows ambient gases to pass into housing 70 but prevents ignition of flammable gas in the surrounding environment by the hot elements. Such catalytic gas sensors are usually mounted in instruments which, in some cases, must be portable and, therefore, carry their own power supply. It is, therefore, desirable to minimize the power consumption of a catalytic gas sensor.

In recent years, substantial research effort has been devoted to the development of combustible gas detectors using semiconductor technology and silicon micromachining. Although the typical electrical power dissipation of conventional catalytic gas sensors is on the order of 250 to 700 mW, miniature, integrated catalytic gas sensors having electrical power consumption on the order of 100 mW and less are under development. See Krebs, P. and Grisel, A., "A Low Power Integrated Catalytic Gas Sensor," *Sensors and Actuators B*, 13–14, 155–158 (1993).

In general, the overall electronic control circuit design of these microsensors is very similar to that of conventional combustible gas sensors. In that regard, such a microsensor is typically provided with both a catalytically active element or detector and a catalytically inactive compensating element or compensator, each of which is used in a measurement circuit such as a Wheatstone bridge circuit. The detector and compensator may be disposed upon a microheater chip, which is disposed upon a substrate.

In both conventional sensors and in microsensors, the catalytic element and the compensating element are expensive to produce. Together, the pair typically accounts for well over half of the cost of the sensor's manufacture. It is desirable, therefore, to develop sensors and methods in which conventional compensating elements are eliminated.

SUMMARY OF THE INVENTION

The present invention provides a combustible gas sensor including an active element in electrical connection with a measurement circuit. The measurement circuit includes a thermistor network to compensate for the effect of changes in ambient temperature to the resistance of the active element. Typically, a thermistor network includes a thermistor and at least one resistor. However, if the thermistor is optimally matched to the thermal response characteristics of the active element, no resistor may be required.

The thermistor network can include a first resistor in series electrical connection with the thermistor and a second resistor in parallel electrical connection with the thermistor to, for example, adjust the output of the thermistor network in compensating for changes in ambient temperature.

In one aspect, in which the resistance of the thermistor increases with increasing temperature, the thermistor can be in one leg of a bridge circuit and the active element can be in another leg of the bridge circuit. The bridge circuit can, for example, be a Wheatstone bridge circuit. In another aspect, in which the resistance of the thermistor decreases with increasing temperature, the thermistor network can be placed in series connection with the active element.

As the geometric surface area of the active element is reduced, the effect of heat lost by thermal conduction from the active element upon the output of the active element decreases. Preferably, for a sensor operating in a temperature range of approximately 400° C. to approximately 600° C., the geometric surface area of the active element is no greater than approximately 0.5 mm². More preferably, the geometric surface area of the active element is no greater than approximately 0.3 mm$^2$. Sensors operating at a temperature lower than approximately 400° C. can have a greater geometric surface area greater than set forth above without excessive heat loss by thermal conduction. In general, increasing activity of the catalyst upon the active element enables operation at a lower temperature.

Preferably, the loss from thermal conduction in the sensors of the present invention is less than approximately 10% of the heat generated by the reaction catalyzed at the active element at full scale of the sensor. Full scale of the sensor is typically the output of the sensor at the lower explosion level (LEL) of the analyte (5% for methane). More preferably, the loss from thermal conduction in the sensors of the present invention is less than approximately 5% of the heat generated by the catalyzed reaction at full scale of the sensor. Even more preferably, the loss from thermal conduction in the sensors of the present invention is less than approximately 3% of the heat generated by the catalyzed reaction at full scale of the sensor.

In another aspect, the present invention provides a measurement circuit for use in a combustible gas sensor including an active element in electrical connection with a thermistor network as described above.

In another aspect, the present invention provides a combustible gas sensor including an active element having a geometric surface area no greater than approximately 0.5 mm$^2$ in electrical connection with a measurement circuit. The measurement circuit includes a compensator that compensates for the effect of changes in ambient temperature to the resistance of the active element without compensating for heat lost by thermal conduction from the active element. The compensator can include a thermistor as described above. Alternatively or additionally, the compensator can include a sensor for measuring ambient temperature in communication with processor circuitry (for example, a microprocessor or dedicated/hardwired circuitry) that compensates for changes in ambient temperature on the output of the active element. The measurement circuits of the present invention can, for example, measure voltage, current or frequency.

In still another aspect, the present invention provides a method of sensing gas including the steps of: (i) providing a catalytic active element having a geometric surface area sufficiently small such that the effect upon the output of the active element of heat lost from the active element by thermal conduction is relatively small (as described above), and (ii) compensating for only the effect of changes in ambient temperature upon the output of the active element.

By eliminating the need for of a conventional compensating element (in both conventional sensors and in microsensors), the present invention greatly reduces the cost of the sensor's manufacture without sacrificing accuracy in the measurement of gas concentration. As used herein, the term "gas sensor" refers generally to both conventional sensors and to microsensors.

DETAILED DESCRIPTION OF THE INVENTION

In the combustible gas sensors of the present invention, expensive compensating elements are eliminated. In several embodiments, such compensating elements are replaced with an inexpensive thermistor network. In general, a thermistor is an inexpensive, commercially available resistor made of materials having resistance that vary rapidly and predictably with temperature. The resistance of a thermistor may either increase or decrease as temperature increase. In the present invention, a thermistor is used to provide the ambient temperature compensating function of a conventional compensating element. As discussed in greater detail below, for catalytic elements of limited geometric or external surface area, accurate measurements of analyte gas concentration can be made while compensating only for ambient temperature changes.

Figure 1A:
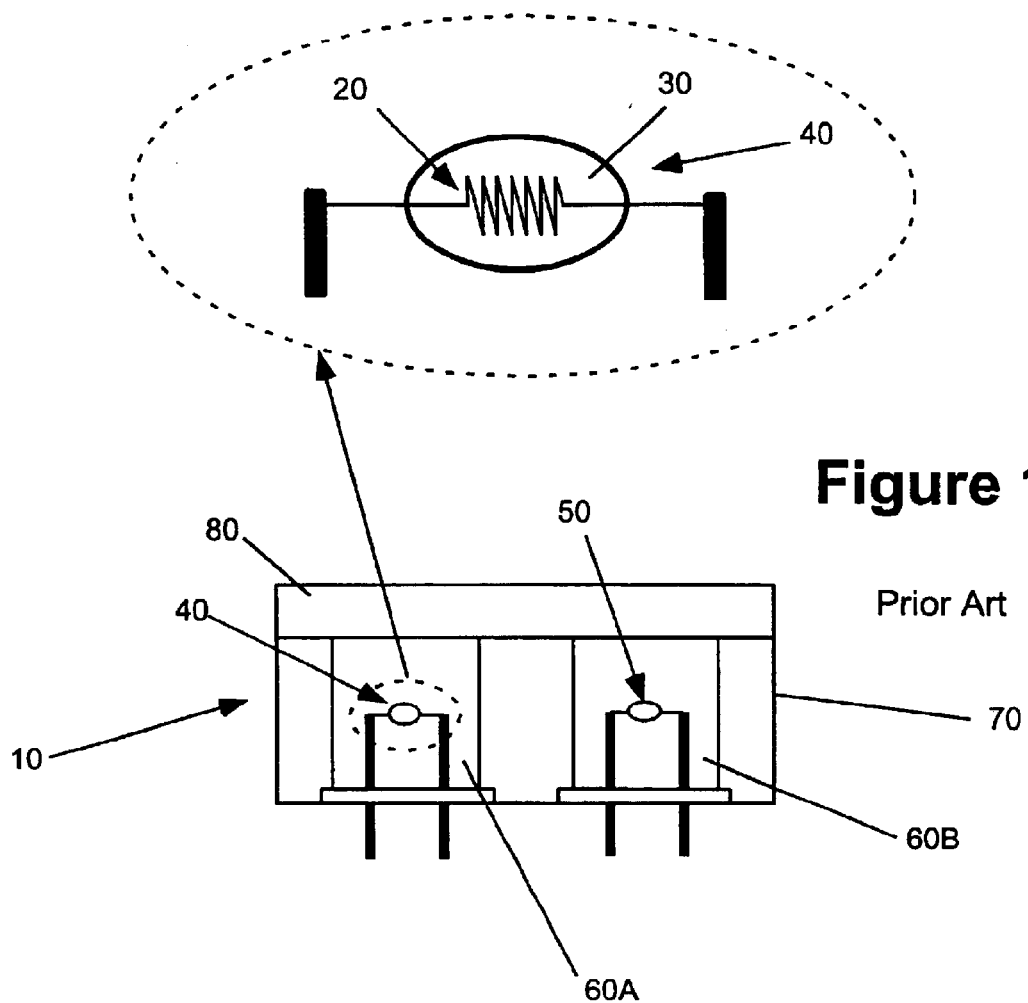
FIG. 1A illustrates a cross-sectional view of a design of a currently available combustible gas sensor.
Figure 1B:
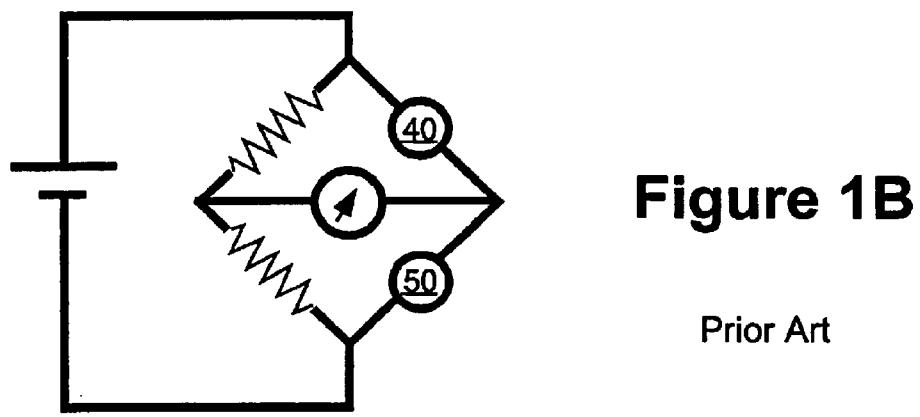
FIG. 1B illustrates the measurement circuitry of the combustible gas sensor of FIG. 1A.
Figure 2A:
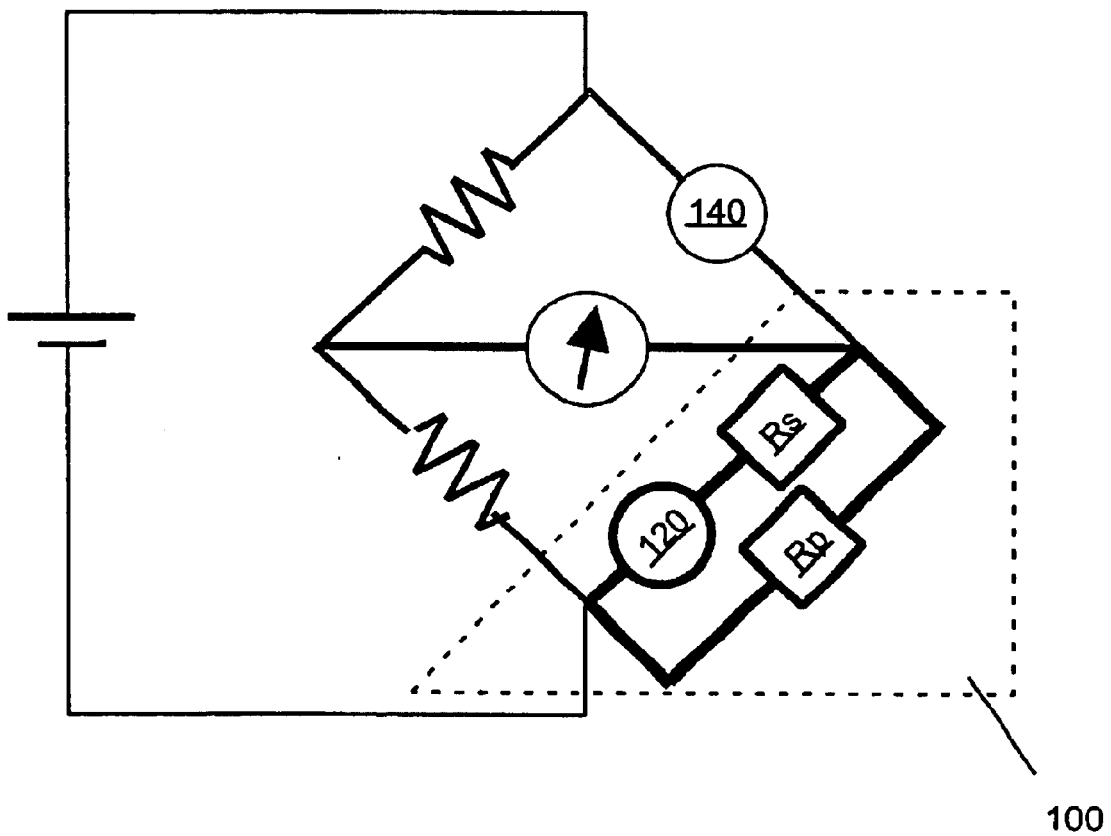
FIG. 2A illustrates an embodiment of a measurement circuit of a sensor of the present invention including a thermistor network in which the resistance of the thermistor increases with increasing temperature.
Figure 2B:
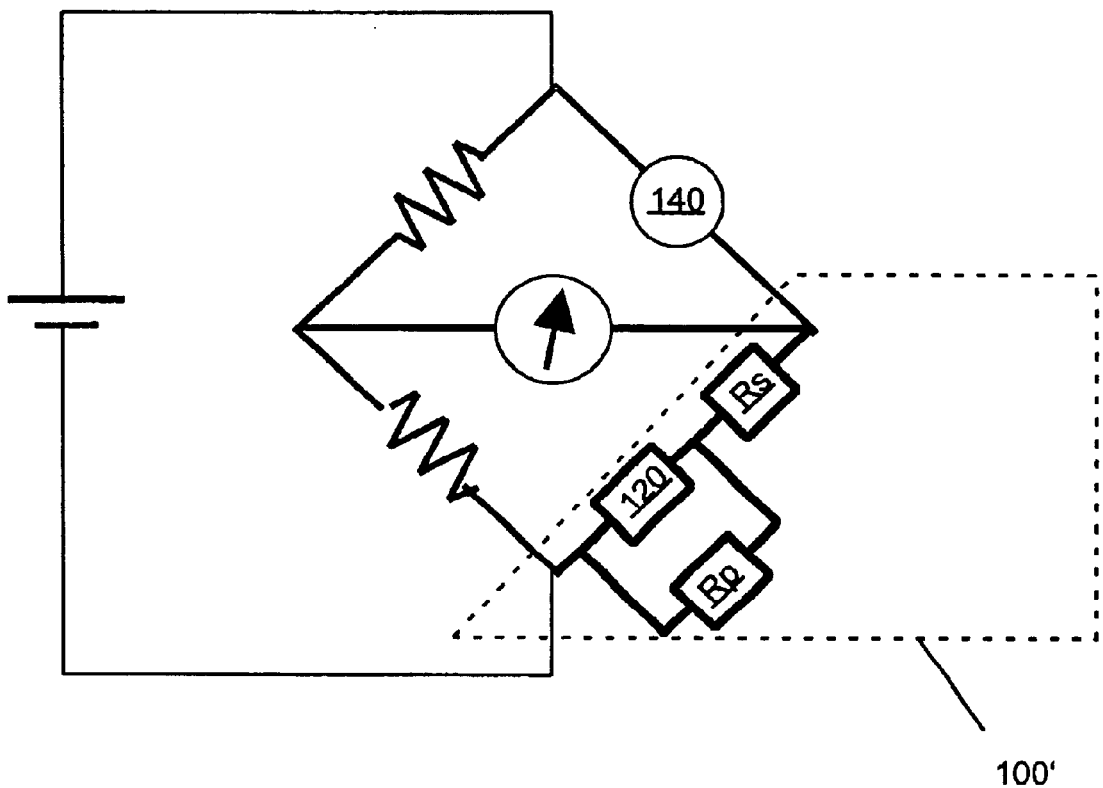
FIG. 2B illustrates another embodiment of a measurement circuit of a sensor of the present invention including a thermistor network in which the resistance of the thermistor increases with increasing temperature.

In the case of a thermistor network, the configuration of the measurement circuitry of the present invention depends upon the direction (that is, directly or inversely) that the thermistor's resistance changes as a function of temperature. In FIGS. 2A and 2B, a thermistor 120 in which resistance increases with increasing temperature (which is the same direction of change as typical catalytic elements and compensating elements), is used in thermistor network 100 or 100' (shown encompassed by dashed lines in FIG. 2A and FIG. 2B, respectively). Thermistor network 100 or 100' can be substituted directly for the compensating element in, for example, a Wheatstone bridge.

Thermistor networks 100 and 100' include thermistor 120, a serial resistor Rs and a parallel resistor Rp. Serial resistor Rs and a parallel resistor Rp are used to fine tune the temperature response of thermistor network 100 to match the response of catalytic element 140.

For a thermistor in which resistance decreases as temperature increases (the direction opposite of typical catalytic elements and compensating elements), a thermistor network such as thermistor network 200 or 200' (shown encompassed by dashed lines in FIG. 3A and FIG. 3B, respectively) is preferably placed in series with a catalytic element 240. As discussed above, a thermistor 220, a serial resistor Rs' and a parallel resistor Rp' can be used to fine tune the temperature response of thermistor networks 200' and 200' to match the response of catalytic element 240.

No attempt was made to optimize the choice of thermistor 120 or thermistor 220' in the thermistor networks of FIGS. 2A through 3B. It is possible to sufficiently closely match the temperature dependence of the resistance of a particular thermistor to the temperature dependence of the resistance of the corresponding active element that one or both of the "adjusting" resistors (for example, Rs and Rp of FIGS. 2A and 2B) described in connection with these embodiments are not necessary.

Figure 3A:
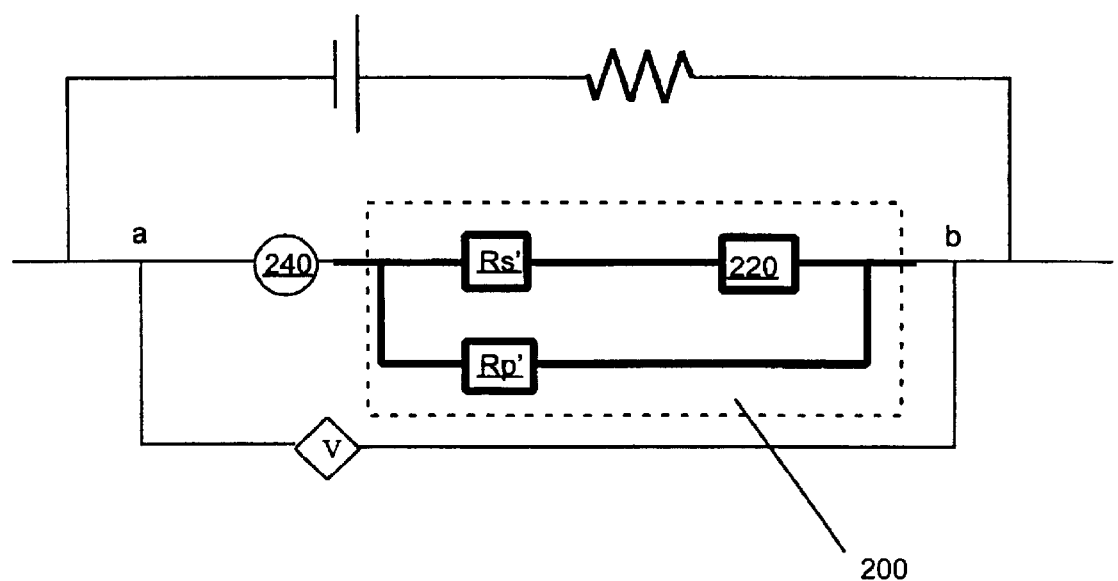
FIG. 3A illustrates an embodiment of a measurement circuit of a sensor of the present invention including a thermistor network in which the resistance of the thermistor decreases with increasing temperature.
Figure 3B:
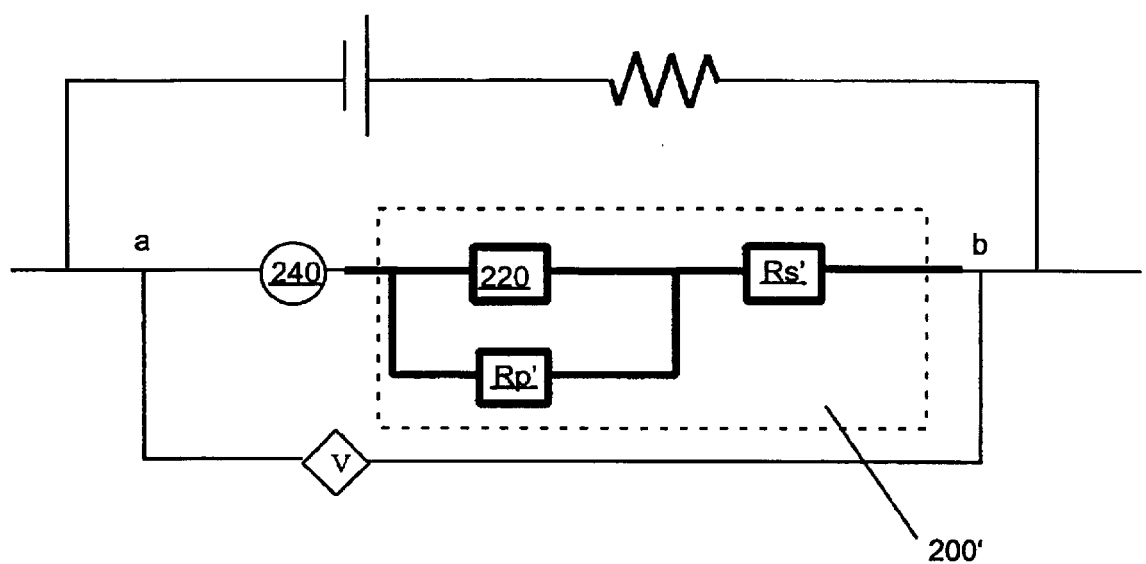
FIG. 3B illustrates another embodiment of a measurement circuit of a sensor of the present invention including a thermistor network in which the resistance of the thermistor decreases with increasing temperature.

In several experiments with a combustible gas sensor including the measurement circuitry configuration of FIG. 3A, an 18 ohm (at room temperature) catalytic element was used in line with a thermistor network including a 100 ohm thermistor 220' available from Betatherm Corporation of Shrewsbury, Mass., and two trim resistors (Rs'=100 ohms, Rp'=20 ohms). Resistance values of series resistor Rs' and parallel resistor Rp' were chosen to make the response of the thermistor network 200 to ambient temperature changes generally equal to, but opposite in sign of, the response of catalytic element 240 to ambient temperature changes.

A 55 mA current was applied from point a to point b and the overall voltage change (V) was monitored. At 25° C., the voltage of the circuit in clean air was 3.2561V. Exposed to 2.5% methane in air (half of the full scale of the sensor of these experiments) at 25° C., the voltage was 3.4582V. The difference (3.4582V–3.2561V) of 0.2021V or 202.1 mV was the signal resulting from methane (at half of full span). The circuit's voltage in air was then measured at a series of ambient temperatures and the differences from the voltage measured at 25° C. were noted as a percentage of full-scale methane voltage (that is, the voltage measured for 5% methane at 25° C.).

TABLE 1

| Temperature (° C.) | Output in air at 55 mA (V) | Output change relative to 25 C. (% of full scale) | Output change relative to 25 C. (% of full scale) for fixed resistor |
|---|---|---|---|
| −20 | 3.2601 | 1 | −19 |
| −10 | 3.2571 | 0.3 | −11 |
| 25 | 3.2561 | 0 | 0 |
| 40 | 3.2591 | 0.7 | 6 |
| 50 | 3.2640 | 2.0 | 12 |

As the data in the third column of Table 1 illustrate, the voltage changes that occur as ambient temperature is varied are small compared to the full-scale span of the sensor. Moreover, performance can be further improved by more completely characterizing the temperature response of the catalytic element than done in the experiments of Table 1 and selecting a more closely matched thermistor. However, even the "non-optimized" thermistor network of the experiments of Table 1 provides similar, if not better, results than a sensor including a conventional compensating element. Typically, sensor specifications require that sensor output not change more that 3% of full scale as temperature varies from room temp over the range of temperatures set forth Table 1.

In the fourth and last column of Table 1, results of similar experiments, but with a fixed 40 ohm resistor (the approximate hot resistance of catalytic element 240 at 55 mA) in place of thermistor network 200, are set forth. In these experiments, voltage variations become a substantial fraction of full-scale sensor response. These experiments clearly indicate that thermistor network 200 performed well.

As discussed above, a conventional compensating element compensates not only for ambient temperature variations, but also for other effects such as losses by thermal conduction from the active element through the analyte gas adjacent to it. The amount of heat loss from the catalytic element is given by:

$$Q = U \cdot A \cdot \Delta T,$$

where Q is the heat lost from the bead by conduction, U is a "heat transfer coefficient" and $\Delta T$ is the temperature difference between the bead and the analyte gas. U is primarily dependent on (and proportional to) the thermal conductivity of the analyte gas adjacent to the bead. The concepts of heat transfer are discussed in detail in Bird, R. B., et al., *Transport Phenomena*, Wiley, New York (1960).

In the above equation, A is the external, or geometric, surface area of the bead (for example, $4\pi r^2$ in the case of a sphere), as opposed to the bead's internal surface area. Typically, beads or other active elements used in combustible gas sensors have large numbers of internal channels or pores giving rise to a relatively large "internal surface area" that can support many more catalyst molecules than could the external or geometric surface area of a similarly shaped, non-porous bead. Typical porous ceramics such as alumina used for catalytic elements have internal surface areas on the order of 50–200 sq. meters/g.

The above equation indicates that if the thermal conductivity of the analyte gas mixture increases, the catalytic bead loses heat. This heat loss cools the bead, causing its resistance, and signal voltage, to drop. The impact of this conductive heat loss can be reduced by reducing the size or area A of the catalytic bead.

An important variable associated with thermal conductivity effects is ambient Relative Humidity (RH). The experiments of Table 2 show the magnitude of the response of catalytic bead output in air as RH (at 25° C.) changes from 10% to 90%, expressed as a percentage of full scale catalytic element output, for catalytic elements of different external surface area.

TABLE 2

| Catalytic element | Approximate Operating Temperature (° C.) | Approximate External Surface Area (sq mm) | Output change 10% to 90% RH (% of full scale) |
|---|---|---|---|
| A | 500 | 0.3 | −1 |
| B | 500 | 0.5 | −3 |
| C | 500 | 0.6 | −3.5 |
| D | 600 | 2.0 | −6.5 |

As expected, output decreases as RH increases. Above approximately 300° C., the thermal conductivity of water is larger than that of air. Moreover, humidity sensitivity was found to increase with increasing external surface area, especially among catalytic elements operating at 500° C.

Sensor specifications for RH sensitivity are typically on the order of +/−3% of full scale. RH sensitivity standards are set forth, for example, in European standard EN50056/7 and Canadian standard CSA C22.2 No. 152M. If the catalytic element has a sufficiently small external or geometric surface area, the sensor will have an acceptably small RH response without compensation for changes in RH. The thermistor networks of the present invention do not respond to or compensate for RH changes. Therefore, while the thermistor networks of the present invention can be used in a sensor with any size of catalytic element, the catalytic element preferably has an external or geometric surface area no greater than approximately 0.5 mm². More preferably, he catalytic element has an external or geometric surface area no greater than approximately 0.3 mm². The thermistor networks of the present invention are particularly suited for use in microsensors in which the external or geometric surface area of the catalytic elements is often no greater than 0.1 mm². Microsensors suitable for use in the present invention are disclosed in U.S. Pat. No. 5,599,584 entitled Microminiature Combustible Gas Sensor and Method of Fabricating a Microminiature Combustible Gas Sensor, assigned to the assignee of the present invention, the disclosure of which is incorporated herein by reference.

Figure 4:
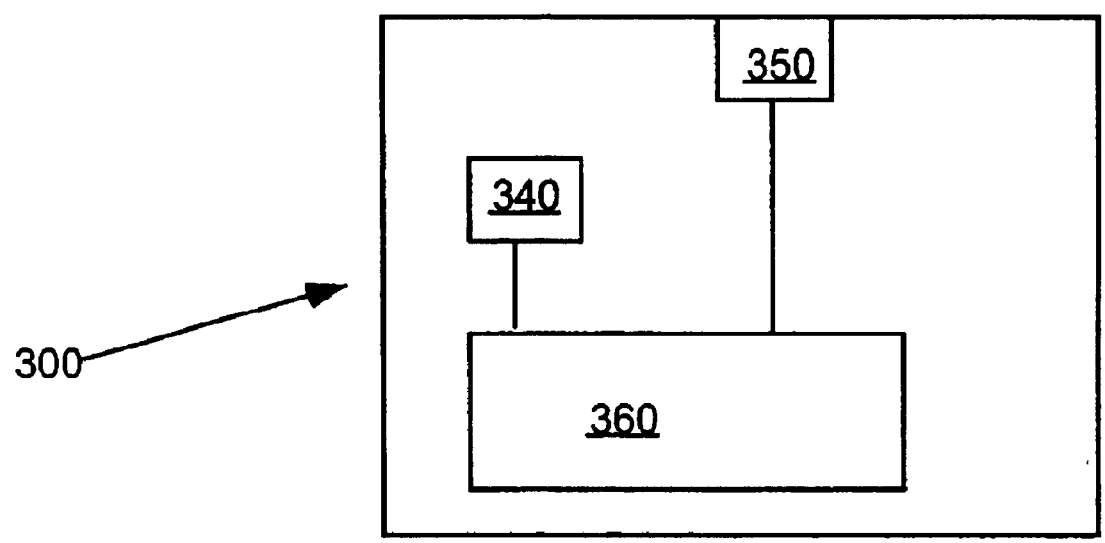
FIG. 4 illustrates another embodiment of a sensor of the present invention.

In a sensor having catalytic element with a relatively small geometric surface area, compensation for changes in temperature without use of an expensive compensating element can also be accomplished in manners other than through use of a thermistor network as described above. For example, FIG. 4 illustrates a catalytic gas sensor 300 including an active element 340, a sensor 350 for measuring ambient temperature and processor circuitry 360. The output of active element 340 is preferably first characterized as a function of changes in ambient temperature. This output can be recorded, for example, as a data table stored in memory of a microprocessor 360 or characterized by an algorithm stored in memory of microprocessor 360. Ambient temperature data is provided to microprocessor 360 by sensor 350. Using the ambient temperature data, processor 360 (or, alternatively, dedicated circuitry) can account/compensate for effects of changes in ambient temperature upon the output received from active element 340.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A combustible gas sensor comprising: a catalytically active element in electrical connection with a measurement circuit, the measurement circuit including a thermistor network to compensate for the effect of changes in ambient temperature to the resistance of the catalytically active element.

2. The combustible gas sensor of claim 1 wherein the thermistor network includes a thermistor and at least one resistor.

3. The combustible gas sensor of claim 2 wherein the thermistor network includes a first resistor in series electrical connection with the thermistor and a second resistor in parallel electrical connection with the thermistor.

4. The combustible gas sensor of claim 3 wherein the resistance of the thermistor increases with increasing temperature, the thermistor being in one leg of a bridge circuit and the active element being in another leg of the bridge circuit.

5. The combustible gas sensor of claim 3 wherein the resistance of the thermistor decreases with increasing temperature and the thermistor network is in serial electrical connection with the active element.

6. A measurement circuit for use in a combustible gas sensor, the measurement circuit comprising: a catalytically-active element in electrical connection with a thermistor network adapted to compensate for the effect of changes in ambient temperature to the resistance of the catalytically-active element without compensating for heat lost by thermal conduction from the catalytically-active element.

7. The measurement circuit of claim 6 wherein the thermistor network includes a thermistor and at least one resistor.

8. The measurement circuit of claim 7 wherein the thermistor network includes a first resistor in series electrical connection with the thermistor and a second resistor in parallel electrical connection with the thermistor.

9. The measurement circuit of claim 7 wherein the resistance of the thermistor increases with increasing temperature, the thermistor being in one leg of a bridge circuit and the active element being in another leg of the bridge circuit.

10. The measurement circuit of claim 7 wherein the resistance of the thermistor decreases with increasing temperature and the thermistor network is in serial electrical connection with the active element.

11. The measurement circuit of claim 6 wherein heat loss from thermal conduction is less than approximately 10% of the heat generated by a reaction catalyzed at the catalytically-active element at full scale.

12. The combustible gas sensor of claim 1 wherein the thermistor network comprises a thermistor.

13. The measurement circuit of claim 6 wherein the thermistor network comprises a thermistor.

14. The combustible gas sensor of claim 2 wherein the thermistor network includes a first resistor in series electrical connection with the thermistor and a second resistor in parallel connection with the thermistor and the first resistor.

15. The measurement circuit of claim 7 wherein the thermistor network includes a first resistor in series electrical connection with the thermistor and a second resistor in parallel connection with the thermistor and the first resistor.

16. The combustible gas sensor of claim 14 wherein the resistance of the thermistor increases with increasing temperature, the thermistor being in one leg of a bridge circuit and the active element being in another leg of the bridge circuit.

17. The combustible gas sensor of claim 14 wherein the resistance of the thermistor decreases with increasing temperature and the thermistor network is in serial electrical connection with the thermistor.

18. The measurement circuit of claim 15 wherein the resistance of the thermistor increases with increasing temperature, the thermistor being in one leg of a bridge circuit and the active element being in another leg of the bridge circuit.

19. The measurement circuit of claim 15 wherein the resistance of the thermistor decreases with increasing temperature and the thermistor network is in serial electrical connection with the thermistor.

20. The measurement circuit of claim 11 wherein heat loss from thermal conduction is less than approximately 5% of the heat generated by a reaction catalyzed at the active element at full scale.

* * * * *